US012802225B2

(12) United States Patent
Yan

(10) Patent No.: US 12,802,225 B2
(45) Date of Patent: Nov. 17, 2026

(54) INTEGRATED AI-POWERED WEARABLE DEVICE AND RETINAL IMAGING SYSTEM FOR EARLY HOME-BASED SCREENING AND DETECTION OF OCULAR TUMORS

(71) Applicant: Ethan Yan, Burlingame, CA (US)

(72) Inventor: Ethan Yan, Burlingame, CA (US)

( * ) Notice: Subject to any disclaimer, the term of this patent is extended or adjusted under 35 U.S.C. 154(b) by 0 days.

(21) Appl. No.: 19/350,655

(22) Filed: Oct. 6, 2025

(65) Prior Publication Data

US 2026/0253215 A1 Aug. 27, 2026

Related U.S. Application Data

(60) Provisional application No. 63/761,978, filed on Feb. 23, 2025.

(51) Int. Cl.
*G06T 7/00* (2017.01)
*A61B 3/00* (2006.01)
(Continued)

(52) U.S. Cl.
CPC .......... *G06T 7/0012* (2013.01); *A61B 3/0025* (2013.01); *A61B 3/0041* (2013.01); (Continued)

(58) Field of Classification Search
CPC ......... G06T 7/0012; G06T 2207/30041; G06T 2207/30096; A61B 3/00; G06V 10/82
See application file for complete search history.

(56) References Cited

U.S. PATENT DOCUMENTS 10,482,603 B1 * 11/2019 Fu ............................ G06N 3/09
2012/0229617 A1 * 9/2012 Yates ................... A61B 3/1208
348/78

(Continued)

FOREIGN PATENT DOCUMENTS

EP 3895616 A1 * 10/2021 ............. H05B 45/10
WO WO-2019087209 A1 * 5/2019 ............... A61B 3/12
WO WO-2025117574 A1 * 6/2025 ........... G06V 40/197

OTHER PUBLICATIONS

Benjamin Moon, Glory Linebach, Angelina Yang, Samantha K. Jenks, Michele Rucci, Martina Poletti, and Jannick P. Rolland, "High refresh rate display for natural monocular viewing in AOSLO psychophysics experiments," Opt. Express 32, 31142-31161 (2024). (Year: 2024).*

(Continued)

*Primary Examiner* — SJ Park
*Assistant Examiner* — Jacqueline R Zak

(57) ABSTRACT

The RetinAI invention provides a novel integrated system designed for home-based early screening and detection of ocular tumors and retinal diseases, leveraging advanced artificial intelligence and optical imaging technology. The system comprises a wearable headset with precisely aligned imaging sensors and dual-mode illumination sources for capturing extraocular images to detect leukocoria and intraocular retinal images for direct visualization of tumors, eliminating the need for pharmacological pupil dilation. On-device deep learning models, including representative object detectors and convolutional neural networks, provide real-time diagnostic outputs. Clinical validations demonstrate RetinAI's capability to detect leukocoria as small as 1 mm in diameter and identify a broad spectrum of retinal diseases, confirming its significant potential to enhance ocular health screening, particularly in underserved and resource-limited settings. The cost-effective, user-friendly, and portable nature of the RetinAI system positions it as an essential tool for improving access to ophthalmic care globally.

9 Claims, 7 Drawing Sheets

(51) Int. Cl.
*A61B 3/15* (2006.01)
*G06V 10/82* (2022.01)
*G16H 30/40* (2018.01)

(52) U.S. Cl.
CPC .............. *A61B 3/152* (2013.01); *G06V 10/82* (2022.01); *G16H 30/40* (2018.01); *G06T 2207/30041* (2013.01); *G06T 2207/30096* (2013.01)

(56) References Cited

U.S. PATENT DOCUMENTS

| | | | | |
|---|---|---|---|---|
| 2019/0189292 | A1* | 6/2019 | Shaya | G16H 30/20 |
| 2020/0409690 | A1* | 12/2020 | Rouland | H04L 9/0637 |
| 2024/0402497 | A1* | 12/2024 | Dave | G02C 11/10 |
| 2025/0035961 | A1* | 1/2025 | Peyman | G02B 3/14 |
| 2025/0228455 | A1* | 7/2025 | Manquez Hatta | A61B 3/14 |

OTHER PUBLICATIONS

Abdolvahabi, A. (2013). Colorimetric and longitudinal analysis of leukocoria in recreational photographs of children with retinoblastoma. PloS one, 8(10), e76677. (Year: 2013).*

I. P. Sari. "Leukocoria Identification: A 5-Fold Cross Validation CNN and Adaboost Hybrid Approach," 2023 6th International Seminar on Research of Information Technology and Intelligent Systems (ISRITI), Batam, Indonesia, 2023, pp. 486-491 (Year: 2023).*

* cited by examiner

INTEGRATED AI-POWERED WEARABLE DEVICE AND RETINAL IMAGING SYSTEM FOR EARLY HOME-BASED SCREENING AND DETECTION OF OCULAR TUMORS

CROSS-REFERENCE TO RELATED APPLICATIONS

This application claims the benefit of U.S. Provisional Patent Application No. 63/761,978, filed on Feb. 23, 2025, which is incorporated herein by reference in its entirety.

STATEMENT OF FEDERALLY SPONSORED RESEARCH

No federal grants or contracts supported the research or development disclosed in this application.

BACKGROUND

Field of Invention

The present invention relates to ophthalmic medical devices and systems, and more particularly to an integrated, low-cost wearable headset and non-mydriatic retinal imaging system with onboard artificial intelligence for early home- and clinic-based screening and detection of ocular tumors and retinal disease. This system is particularly suited for detecting leukocoria and intraocular retinal abnormalities, notably retinoblastoma, without the requirement of pharmacological pupil dilation, thereby improving accessibility and effectiveness of routine ocular health assessments and significantly facilitating early disease intervention.

Description of Related Art

Vision impairment is a widespread health problem, and in children the most consequential ocular tumor is retinoblastoma, which often first appears as leukocoria. Early detection is critical, yet routine screening still depends on ophthalmoscopic red-reflex exams and dilated fundus imaging that typically require trained specialists, clinic-grade optics, and pharmacologic mydriasis. These dependencies limit access and repeatability in homes, schools, and primary-care settings.

Non-mydriatic fundus cameras reduce reliance on pupil dilation but remain expensive and are generally designed for specialist workflows. Lower-cost prototypes often involve lens stacks and procedures that are difficult for non-experts to execute reliably, which constrains widespread deployment outside ophthalmology clinics.

Smartphone-based leukocoria tools have been proposed, but they are sensitive to small changes in angle and lighting between the flash, camera, and pupil; computational "red-eye" suppression can attenuate the very reflex being measured; and reported sensitivities skew toward later disease. As a result, these approaches can be inconsistent precisely where early detection is most needed.

Artificial-intelligence studies report strong performance on retrospective image sets, yet most assume clinic-quality images acquired under controlled geometry, perform inference off-device, and do not address capture guidance for lay users. Accordingly, there remains a need for an integrated, low-cost system that enforces coaxial alignment between illumination and camera for extraocular screening, uses infrared preview with a synchronized white-light exposure to obtain color fundus images without pharmacologic dilation, and executes on-device detection and classification with immediate, explainable outputs in a modular form factor operable by non-specialists.

SUMMARY OF THE INVENTION

In one aspect, an ocular screening system is provided that operates in two coordinated modes. A first, extraocular mode employs a wearable headset that constrains an imaging sensor and an illumination assembly so that both are substantially coaxial with a subject's eye, thereby producing repeatable pupil images for automated leukocoria detection. A second, retinal mode employs a non-mydriatic imaging assembly in which infrared preview is used to frame the fundus without inducing pupillary constriction and a timed white-light exposure synchronized to the camera shutter is used to obtain a color retinal image for automated analysis. In representative implementations, a single electronics core services both modes.

In another aspect, a computing module controls exposure, focus, and illumination timing; executes trained computer-vision models including object detectors and image classifiers to identify leukocoria, optic discs, and retinal tumors; and presents alignment guidance and diagnostic outputs on a local display. In certain embodiments, the computing module further computes color-space statistics within a pupil region to assist in distinguishing normal reflexes from leukocoria, provides on-device inference for privacy and latency, and optionally encrypts and transmits data for telemedicine review. The software and analytics may execute on embedded processors or on a host smartphone while the disclosed mechanics maintain coaxial alignment.

In further aspects, a modular mechanical design allows rapid conversion between modes by attaching a headset shell or an optical extension that positions a diopter lens on the same optical axis as the illumination assembly and the imaging sensor. The modules include quick-attach mounts that fix working distance and alignment to simplify operation by non-specialists. Safety features may limit illumination intensity and exposure duration, and user-assistance features may include visual or audible prompts, exposure autotuning, and pediatric or adult fit adjustments. The disclosed configurations enable low-cost manufacture with additively fabricated components while maintaining repeatable imaging geometry suited to early screening.

In yet another aspect, methods are provided for screening a subject for ocular disease, comprising: aligning a wearable headset so that an illumination assembly and an imaging sensor are substantially coaxial with an eye; capturing at least one extraocular image of a pupil; processing the image to determine a presence or absence of leukocoria; attaching a diopter-lens module; previewing the fundus under infrared illumination; actuating a synchronized white-light exposure to acquire a color retinal image; processing the retinal image to localize or classify abnormalities; and presenting a result on the device. In some implementations, the system detects simulated leukocoria of small diameters and localizes retinal tumors in captured fundus images, demonstrating feasibility for pre-screening in homes, schools, and primary care. These results are provided as non-limiting examples supporting enablement.

In a further aspect, a non-transitory computer-readable medium stores instructions that, when executed by one or more processors of a device having an illumination assembly, an imaging sensor, and a display, cause the device to control infrared preview and synchronized white-light exposure; acquire extraocular and retinal images; infer leukocoria and retinal abnormalities using object detection and classification models; render alignment cues and explainable outputs on the display; store images and results with timestamps; and, when enabled, encrypt and transmit data to a remote re viewer.

The disclosed system addresses failure modes in prior approaches by enforcing coaxial geometry to reduce angle-dependent variability seen in ad-hoc smartphone photography, by acquiring color fundus images without pharmacologic dilation using infrared preview and shutter-synchronized white-light capture, and by delivering immediate, on-device, explainable results in a modular form factor operable by non-specialists. In representative studies underlying the present disclosure, the headset showed detection of small simulated leukocoria and the retinal module localized tumors while distinguishing the optic disc; these demonstrations are illustrative of utility and do not limit the scope of the claims.

LIST OF REFERENCE NUMERALS

Figure 1:
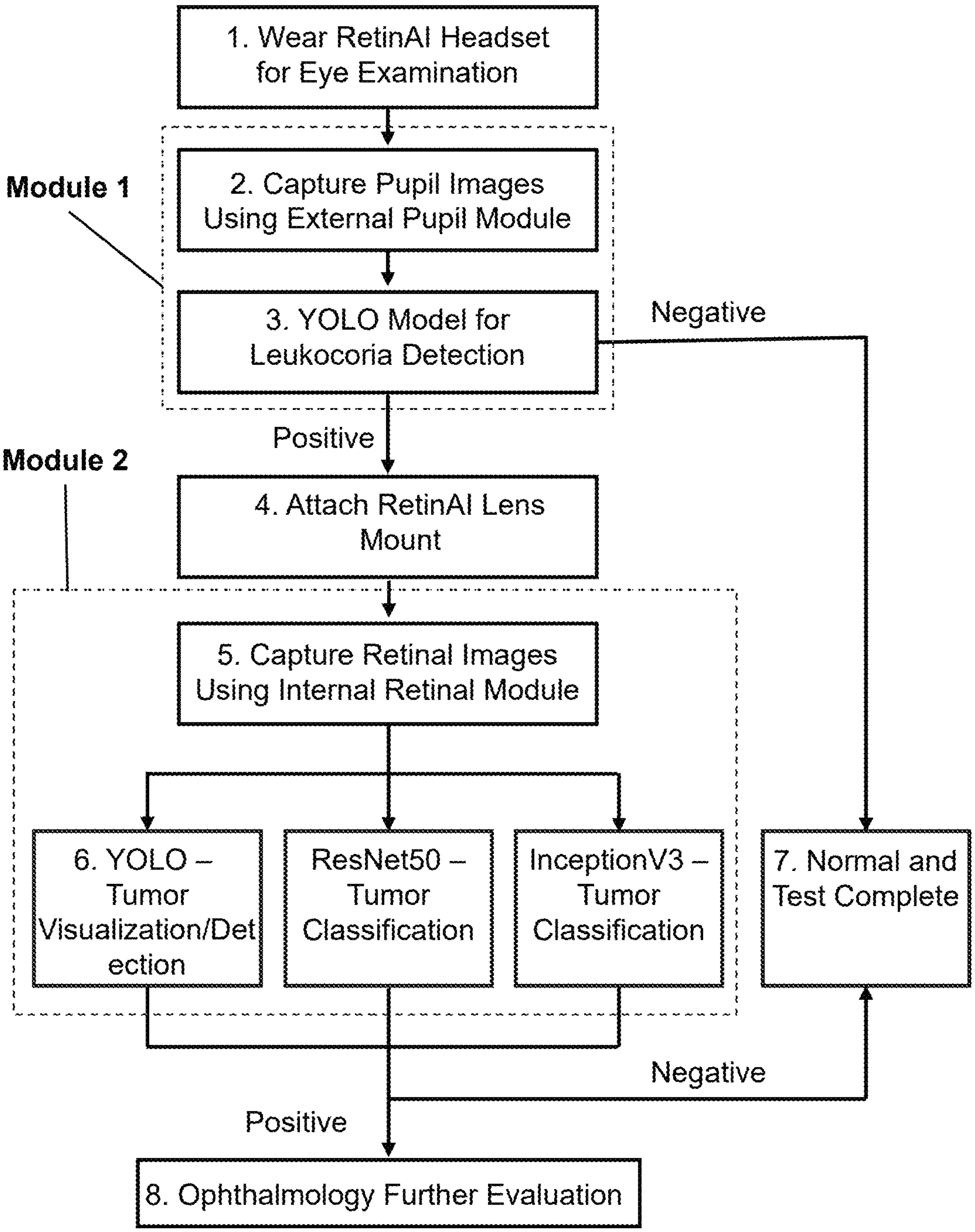
FIG. 1 is a functional flow diagram of a two-module RetinAI pipeline. The sequence shown includes: "Wear RetinAI Headset for Eye Examination"; "Capture Pupil Images Using External Pupil Module"; "YOLO Model for Leukocoria Detection"; "Attach RetinAI Lens Mount"; "Capture Retinal Images Using Internal Retinal Module"; "YOLO-Tumor Visualization/Detection," "ResNet50-Tumor Classification," and "Inception V3-Tumor Classification"; output of "Normal"/"Positive/Negative"; and "Ophthalmology Further Evaluation."

100—Illumination assembly (dual infrared/white LED)
102—Camera (visible and infrared)
103—Front shell of electronics compartment
104—Power bank
106—Embedded processor
108—Display (LCD touchscreen)
110—Subject's eye
112—Headset shell (extraocular)
114—Diopter lens (e.g., 20 diopters)
200—Headset assembly (overall)
210—Outer shell of electronics compartment (exterior housing)
212—Capture button
214—Rear cover
300—Lens-holder bar (optical extension, dual-rod)
302—Lens mount

DETAILED DESCRIPTION

Conventions and Overview

Hereinafter, the integrated extraocular and retinal imaging system described herein is referred to as "RetinAI"; this designation is merely exemplary and not intended to limit the scope of the claimed subject matter. Unless otherwise indicated, like reference numerals denote like elements across the drawings. Positional terms such as "front," "rear," "left," and "right" describe the device as worn by a subject and are used for convenience rather than limitation. The term "non-mydriatic" denotes retinal imaging performed without pharmacologic dilation.

At a high level, the disclosed system operates in two coordinated modes. A first, extraocular mode produces repeatable pupil images for automated leukocoria screening using a coaxial headset that constrains the relative positions of a camera (102) and an illumination assembly (100). A second, retinal mode captures non-mydriatic fundus images using infrared preview followed by a shutter-synchronized white-light exposure, with images analyzed on-device using trained models. The principal blocks and dual-module pipeline are depicted in FIG. 1.

Figure 2:
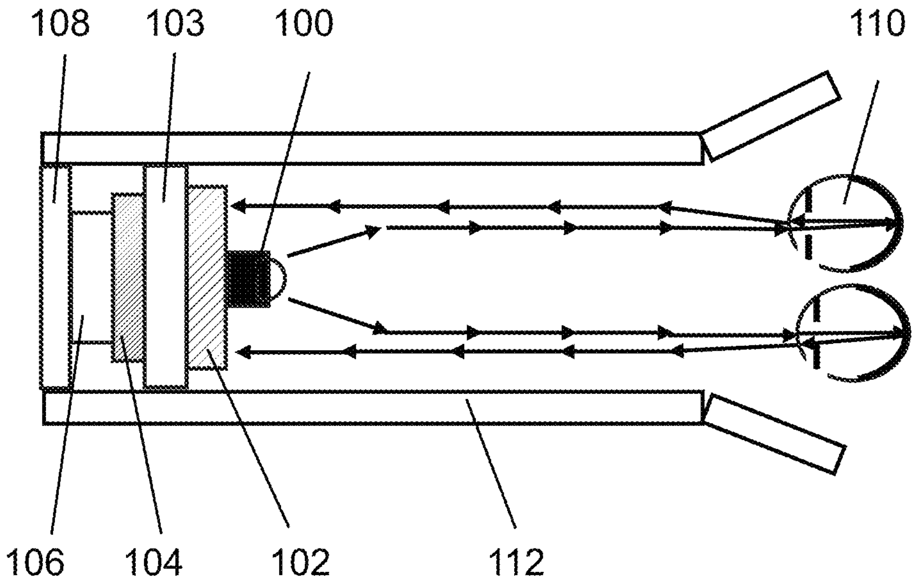
FIG. 2 is a schematic of a wearable extraocular module showing an illumination assembly (100) and a camera (102) arranged with the subject's eye (110), together with a power bank (104), an embedded processor (106), a display (108), and a front shell of electronics compartment (103) retaining these components, a headset shell (112).

In the schematic view of FIG. 2, the term front shell of electronics compartment (103) denotes the front part of the internal enclosure that retains the power supply (104), processor (106), and display (108). The term headset shell (112) denotes the extraocular housing that constrains optical alignment. In the orthographic and exploded views of FIGS. 4-7, the term outer shell of electronics compartment (210) denotes the exterior housing to which the optical extension is mounted.

In representative embodiments, the illumination assembly (100) and camera (102) are aligned such that coaxiality is maintained within about 5 degrees of angular deviation and about 5 millimeters of lateral offset at a working distance of about 40-60 millimeters. These tolerances reproducibly generate the clinical red-reflex geometry for leukocoria screening while preserving focus for non-mydriatic retinal capture when the optical extension is used.

Definitions

As used herein, "artificial intelligence" denotes computational systems that perform detection, classification, or related inference tasks on images captured by the disclosed hardware.

An "object-detection model" denotes a model that outputs locations and categories of structures, including but not limited to leukocoria, optic discs, and tumors; examples include YOLO-type detectors configured for real-time inference on embedded hardware.

A "convolutional neural-network classifier" denotes a model that outputs labels or likelihoods for disease states from a retinal image; examples include ResNet-50 or similar transfer-learned architectures.

A "wearable headset" denotes a shell and associated mounts that hold an illumination assembly and a camera so that both are substantially coaxial with the user's eye;

"Substantially coaxial" means aligned closely enough to reproduce the clinical red reflex reliably in typical use without restricting the invention to a particular tolerance.

"Dual infrared/white LED lights" denote a lighting assembly that provides infrared illumination for preview and white-light illumination for capture.

"Non-mydriatic fundus imaging" denotes retinal capture without the use of pharmacologic pupil-dilating agents and, in the disclosed system, is enabled by infrared preview followed by synchronized white-light exposure.

Reference Numerals and Standardization

Figure 3:
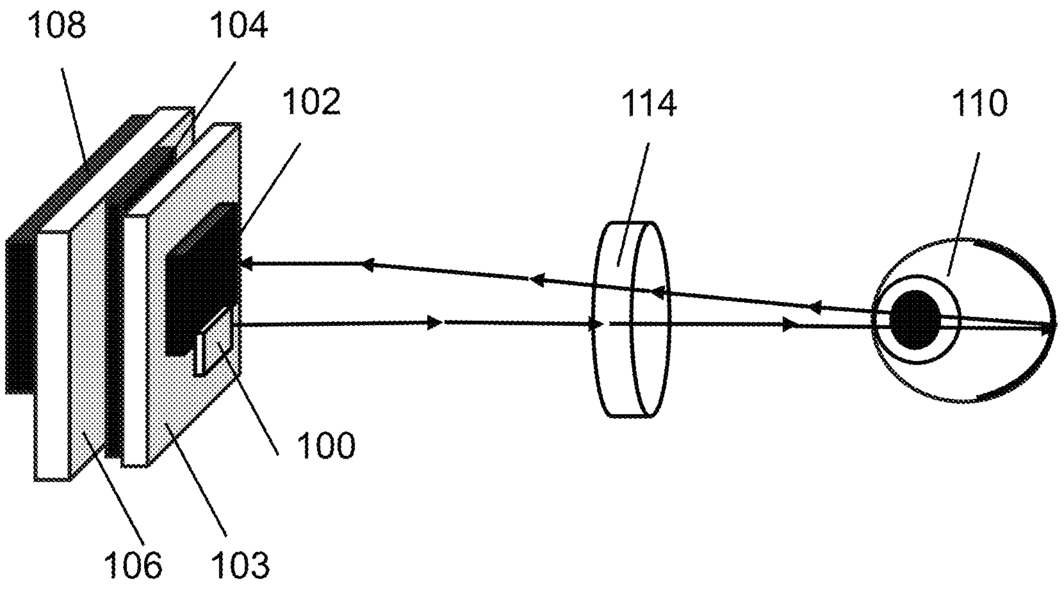
FIG. 3 is a schematic of a retinal imaging module in which a diopter lens (114) is positioned on the optical axis with the camera (102) and illumination assembly (100), together with a power bank (104), an embedded processor (106), a display (108), a front shell of electronics compartment (103), and the subject's eye (110).

Unless otherwise indicated, like reference numerals denote like elements across FIGS. 1-7 of the accompanying drawings. The drawings use the following reference numerals: 100 denotes a dual infrared/white LED illumination assembly illustrated in FIGS. 2-3 and 5-7; 102 denotes a camera module responsive to visible and infrared wavelengths illustrated in FIGS. 2-3, and 5-7; 103 denotes a front shell of electronics compartment that retains the power bank, processor, and display as shown in FIGS. 2-3; 104 denotes a power bank illustrated in FIGS. 2-3, 5, and 7; 106 denotes an embedded processor illustrated in FIGS. 2-3, 5, and 7; 108 denotes a local LCD touchscreen display illustrated in FIGS. 2-3, 5, and 7; 110 denotes the subject's eye illustrated in FIGS. 2-3; 112 denotes a headset shell of the extraocular module illustrated in FIGS. 2 and 4; 114 denotes a diopter lens, for example a 20 diopter lens, illustrated in FIGS. 3, 6, and 7; 200 denotes a headset assembly illustrated in FIG. 4-5; 210 denotes an outer shell of electronics compartment providing the exterior housing illustrated in FIGS. 4-7; 212 denotes a capture button illustrated in FIGS. 4-7; 214 denotes a rear cover illustrated in FIGS. 4-7; 300 denotes a lens-holder bar illustrated in FIGS. 6-7; and 302 denotes a lens mount illustrated in FIGS. 6-7.

Embodiments Keyed to the Figures

Unless otherwise indicated, like reference numerals denote like elements across the figures.

FIG. 1. is a functional flow diagram divided into "Module 1" and "Module 2." In Module 1 the sequence begins with "1. Wear RetinAI Headset for Eye Examination," continues to "2. Capture Pupil Images Using External Pupil Module," and then to "3. YOLO Model for Leukocoria Detection." The diagram next shows "4. Attach RetinAI Lens Mount," after which Module 2 proceeds with "5. Capture Pupil Images Using Internal Retinal Module." The analysis stage is shown with three model blocks—"YOLO—Tumor Visualization/Detection," "ResNet50—Tumor Classification," and "InceptionV3—Tumor Classification." The outcomes branch to "7. Normal and Test Complete" and to "Positive/Negative," with a downstream box labeled "8. Ophthalmology Further Evaluation."

FIG. 2. depicts the wearable extraocular module in schematic form. An illumination assembly (100) and a camera (102) are located on the front shell of the electronics compartment (103), positioned coaxially forward of the subject's eye (110). To the rear of these optical elements, the electronics compartment retains a power bank (104), an embedded processor (106), and a display (108). The overall structure is enclosed within a headset shell (112). This schematic layout illustrates how the illumination assembly (100) and the camera (102) are aligned with the subject's eye (110) within the headset structure to generate repeatable pupil images for leukocoria screening.

FIG. 3. depicts the retinal imaging module in which the diopter lens (114) is placed on the same optical axis as the camera (102) and the illumination assembly (100) located on the front shell of the electronics compartment (103). The schematic further shows the subject's eye (110) opposite the lens, and locates the power bank (104), embedded processor (106), display (108) within the compartment. This view highlights the addition of the diopter lens (114) relative to the extraocular configuration of FIG. 2.

Figure 4:
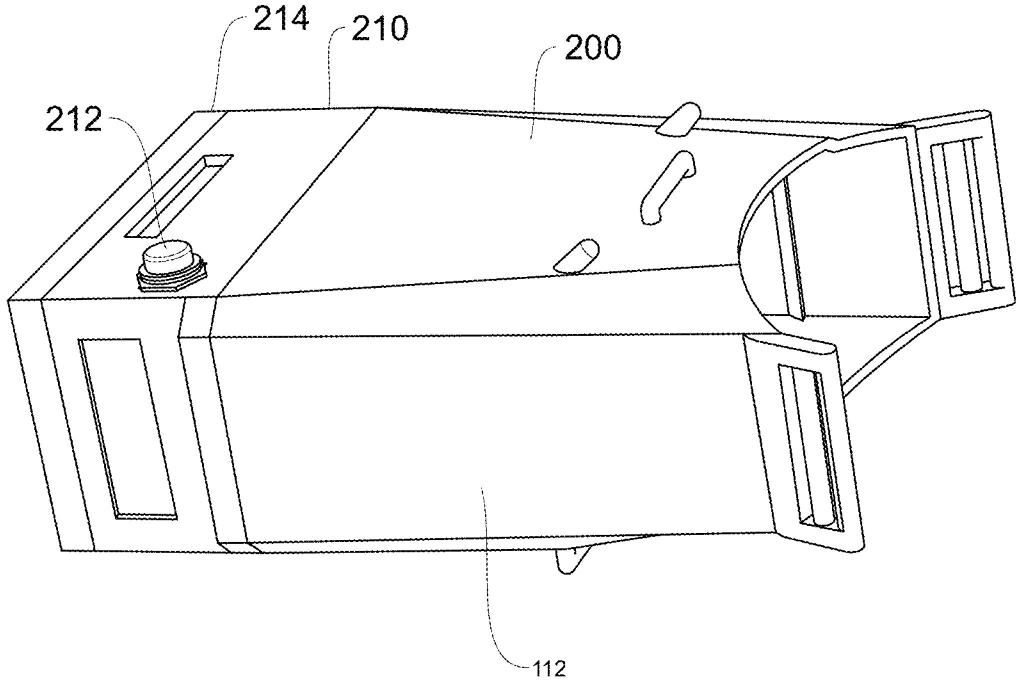
FIG. 4 is an orthographic view of the headset assembly (200), showing a headset shell (112), including an outer shell of an electronics compartment (210), a capture button (212), and a rear cover (214).

FIG. 4. is an orthographic perspective of the headset assembly (200). The outer shell (210) encloses the electronics and supports a capture button (212) on the left-hand surface, while a rear cover (214) closes the housing at the proximal end. The headset shell (112) defines the extraocular module structure. This view illustrates the overall form factor and exterior geometry of the headset as worn.

Figure 5:
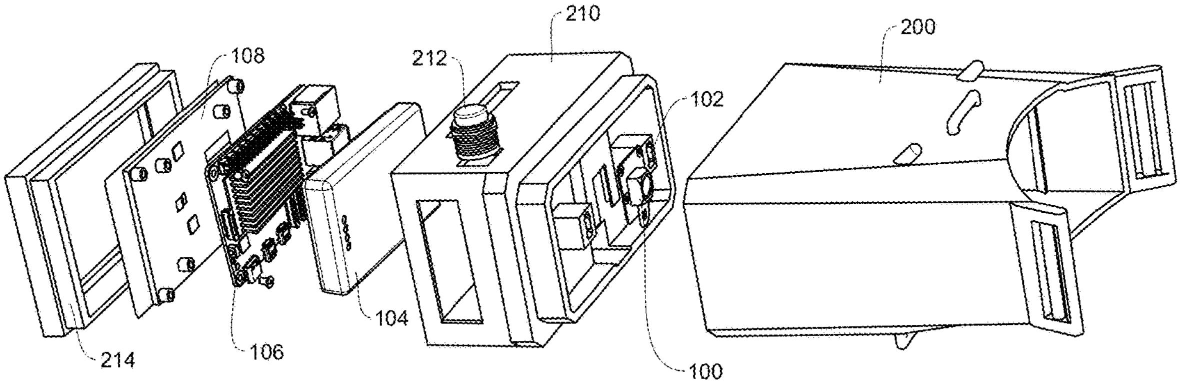
FIG. 5 is an exploded view of the wearable headset module showing subassemblies including a rear cover (214), a display (108), an embedded processor (106), a power bank (104), a capture button (212), an outer shell (210), a camera (102), and an illumination assembly (100), together with the headset assembly (200).

FIG. 5. is an exploded view of the wearable headset module. From left to right, the drawing shows the rear cover (214), the display (108), the embedded processor (106), and the power bank (104). These are followed by the subassembly bearing the capture button (212) and the outer shell (210). At the front of that subassembly, the camera (102) mounts next to the illumination assembly (100). The headset assembly (200) is illustrated at the right to indicate how the front housing mates with the head-worn portion. The figure depicts the order and relationship of the principal parts for assembly.

Figure 6:
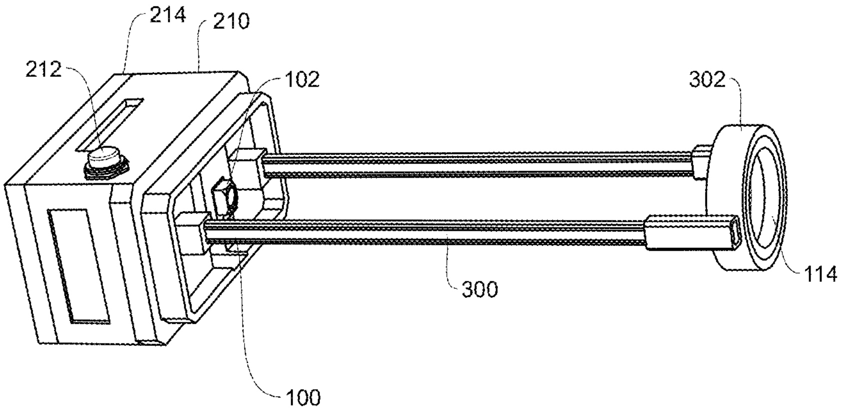
FIG. 6 is a perspective view of an optical extension mounted to the outer shell (210), depicting a capture button (212), a rear cover (214), an illumination assembly (100), a camera (102), a dual-rod lens-holder bar (300), a lens mount (302), and a diopter lens (114)

FIG. 6. shows the retinal image system with an optical extension fitted to the outer shell (210). The extension comprises a dual-rod lens-holder bar (300) extending forward from the housing that carries the illumination assembly (100) and camera (102). The rods terminate in a lens mount (302), supporting a diopter lens (114). The outer shell (210) also supports a capture button (212) and is closed at the rear by a cover (214). The view illustrates the fixed working distance geometry established by the optical extension.

Figure 7:
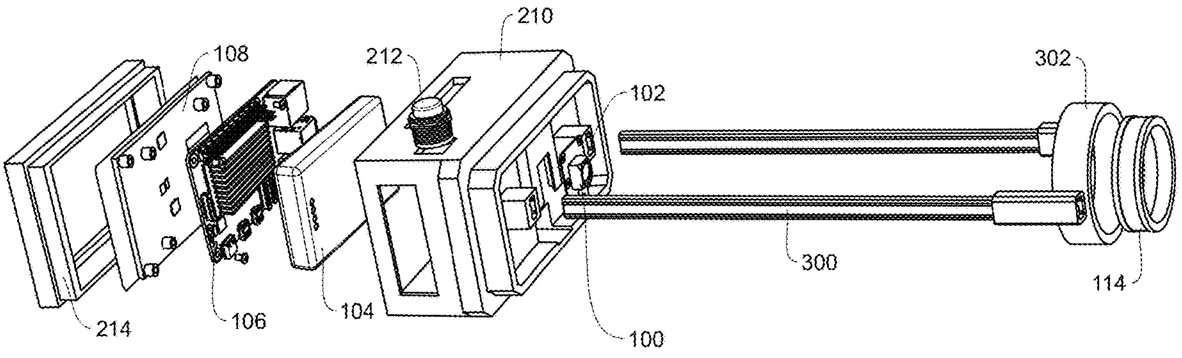
FIG. 7 is an exploded view of an integrated imaging module bearing the optical extension, including headset subassemblies with a rear cover (214), a display (108), an embedded processor (106), a power bank (104), an outer shell (210), a capture button (212), an illumination assembly (100), and a camera (102), together with optical extension components including a lens-holder bar (300), a lens mount (302), and a diopter lens (114).

FIG. 7. is an exploded view of the integrated imaging module with the optical extension. Proceeding from the rear, the drawing shows the rear cover (214), the display (108), and the embedded processor (106), followed by the power bank (104). Forward of these electronics, the outer shell (210) supports the capture button (212), the camera (102), and the illumination assembly (100) at the front face. Extending forward, a dual-rod lens-holder bar (300) terminates in a lens mount (302) that positions the diopter lens (114) at a fixed working distance. This arrangement illustrates how the optical extension maintains alignment and spacing of the lens (114) with respect to the camera (102) and illumination assembly (100).

System Architecture and Operation

The system operates in two coordinated modes, as reflected in the flow of FIG. 1: a first module that acquires extraocular pupil images for leukocoria detection, followed by attachment of a lens mount and operation of a second module that captures retinal images for tumor visualization and classification. On-device inference provides immediate user outcomes at the end of the flow.

In extraocular mode, the illumination assembly (100) and the camera (102) are mounted at the front shell of the electronics compartment unit (103) so that they are substantially coaxial with the subject's eye (110). Immediately to the rear of these optical elements, the electronics compartment retains the power bank (104), the embedded processor (106), and the display (108), enclosed within the outer shell (210). The compartment is further enclosed within a headset shell (112) and closed at the rear by a cover (214). The embedded processor (106) controls camera exposure and gain, drives the illumination assembly (100), and renders alignment cues and inference readouts on the display (108). This enforced coaxial configuration produces a consistent red-reflex geometry and mitigates angle-dependent false negatives typical of ad-hoc smartphone imaging (FIG. 2).

In retinal mode, a diopter lens (114) is introduced on the same optical axis as the illumination assembly (100) and the camera (102). The lens is positioned by an optical extension comprising a dual-rod lens-holder bar (300) and a lens mount (302). The extension couples to the front of the outer shell (210), with a capture button (212) accessible on the housing, the headset shell (112) enclosing the assembly, and the rear cover (214) closing the unit. Under firmware control, infrared preview frames are acquired to center the fundus without provoking pupillary constriction. Pressing the capture button (212) triggers a short white-light pulse from the illumination assembly (100) that is synchronized to the camera (102) exposure, thereby obtaining a non-mydriatic color retinal image through the diopter lens (114). The captured image is rendered on the display (108), stored locally, and processed on-device by the embedded processor (106) for tumor localization and/or classification (FIGS. 3, 6, and 7).

Electronics, Optics, and Firmware Control

Representative embodiments incorporate a camera module (102) responsive to both infrared and visible wavelengths, together with a compact dual infrared/white light emitting diode (LED) illumination assembly (100). Electronic subsystems include an embedded processor (106) configured to execute object-detection and classification models in real time, a capacitive touchscreen display (108) for alignment cues and user feedback, and a rechargeable power bank (104) for portable operation. In one implementation, an image sensor of approximately 11.9 megapixels with infrared sensitivity is employed in conjunction with the dual infrared/white LED source, a single-board computer, and a four- to five-inch liquid crystal display. These electronic components are retained within an internal electronics compartment situated inside the headset assembly. A headset shell (112) constrains the coaxial relationship between the illumination assembly (100), the camera (102), and the subject's eye, while an outer shell (210) provides the exterior housing of the device. Control logic implemented in firmware governs flash timing, exposure, and focus. Exposure durations on the order of 5000 microseconds and a minimum focal distance of approximately five centimeters were sufficient to yield sharp pupil images in testing, although other values may be selected depending on optical configuration.

The optical extension accommodates a diopter lens (114), with a 20-diopter element provided as one illustrative embodiment, while alternative optical powers suitable for indirect ophthalmoscopy are contemplated. The extension is formed by a dual-rod lens-holder bar (300) that terminates in a lens mount (302) coupled to the diopter lens (114), as depicted in FIGS. 6-7. These elements establish a fixed spacing that maintains focus while minimizing overall mass for pediatric use. Internal baffles formed within the outer shell (210) reduce stray glare and improve image contrast. Firmware routines regulate the duty cycle and pulse duration of the illumination assembly (100), operate an infrared preview mode followed by synchronized white-light exposure, and manage capture timing to avoid triggering the pupillary reflex, thereby preserving non-mydriatic retinal imaging.

Software Architecture and On-device Analytics

The embedded processor (106) executes two coordinated analysis pipelines corresponding to the dual-module workflow illustrated in FIG. 1.

In an extraocular pipeline, images of the pupil acquired by the camera (102) under illumination from the assembly (100) are processed by an object detection model trained to distinguish leukocoria from a normal red reflex. The detector generates bounding boxes and associated confidence values. These bounding boxes provide explainability to the user and may also drive alignment cues rendered on the local display (108). The processor (106), power bank (104), and display (108) are retained within an electronics compartment (103), which is enclosed by a headset shell (112) that constrains optical alignment. The housing is completed by an outer shell (210) and a rear cover (214).

In a retinal pipeline, images captured through the diopter lens (114) are analyzed by either (i) a convolutional neural network classifier or (ii) an object detection model. These models operate to classify images as normal or pathological, or to localize structures such as the optic disc and tumors. The optical extension, comprising the lens-holder bar (300), lens mount (302), and associated structures, attaches to the front of the outer shell (210). The capture button (212) remains accessible on the housing, while the rear cover (214) secures the unit. In representative development, classification and detection results were available locally in near real time on the display (108), permitting immediate feedback during examination.

Illustrative performance examples are as follows. A leukocoria detection model trained on curated image sets demonstrated validation metrics including precision, recall, and mean average precision in the mid-90 percent range. Retraining on images with digitally simulated small lesions preserved high mean average precision while maintaining practical sensitivity and specificity. For retinal analysis, classification models such as convolutional neural networks achieved validation accuracies approaching 97 percent, while detection models yielded mean average precision values on the order of 96 percent. These numerical examples are provided to illustrate the utility of the disclosed system and are not intended to limit the claimed subject matter to specific models, parameters, or thresholds.

An optional image-processing module further analyzes pupil crops in the hue-saturation-value (HSV) color space. Distributional statistics of pixel intensities within the cropped region may assist decision-making in varied ambient lighting conditions. Observed separation between normal and leukocoria clusters in HSV space supports the use of this auxiliary module for enhanced decision confidence.

Methods of Use

In leukocoria screening mode, the user dons the headset assembly (200) as shown in FIG. 4. The embedded processor (106), retained together with the power bank (104) and display (108), provides alignment cues on the display while controlling the illumination assembly (100) and the camera (102). Under processor control, the illumination assembly projects light coaxially into the subject's eye (110), and the camera acquires one or more pupil images. The object detection pipeline processes the acquired frames to determine the presence or absence of leukocoria. Bounding box overlays and associated confidence measures are rendered on the display (108) for immediate explainability. The images and metadata are stored in memory under processor control and may be retained locally or transmitted securely for review. The electronics compartment is enclosed by the headset shell (112) that maintains optical alignment, with the outer shell (210) and rear cover (214) completing the assembly (FIG. 2).

In retinal imaging mode, the optical extension shown in FIG. 6 is affixed to the front of the outer shell (210). The extension comprises a dual-rod lens-holder bar (300) terminating in a lens mount (302) that carries the diopter lens (114). With the extension installed, the processor (106) first enables an infrared preview mode through the illumination assembly (100) to allow the examiner to center the fundus without triggering pupillary constriction. Upon actuation of the capture button (212), the processor triggers a white-light pulse from the illumination assembly that is synchronized to the camera (102) exposure. The retinal image obtained through the diopter lens (114) is processed by classification or detection models to localize optic disc and tumor structures, and the results, together with associated confidence measures, are presented immediately on the display (108). Captured images are timestamped and stored with device identifiers for later retrieval (FIG. 7).

Manufacturing and Assembly

Structural components of the system include the headset shell (112), the outer shell (210), the capture button (212), the rear cover (214), the lens-holder bar (300), and the lens mount (302). These parts may be fabricated by additive manufacturing processes using thermoplastics. The exploded assemblies shown in FIGS. 5 and 7 illustrate the order of placement for these elements.

Electronic components comprising the illumination assembly (100), the camera (102), the embedded processor (106), the display (108), and the power bank (104) are retained within an electronics compartment (103), which provides an internal housing for these subsystems. The compartment is situated within the overall headset assembly, enclosed by the headset shell (112) for optical alignment and the outer shell (210) for structural support and exterior finish. The diopter lens (114) is retained within the lens mount (302), and the lens-holder bar (300) establishes a fixed working distance between the diopter lens (114) and the camera/illumination axis, thereby maintaining focus while preserving structural rigidity.

Calibration and Quality Control

Each assembled unit may undergo calibration to confirm optical coaxiality and imaging performance. Optical alignment can be verified by capturing an image of a printed target and calculating the offset between the corneal reflection and the optical axis of the camera (102). Any measured deviation may be stored as a per-unit correction factor in device memory.

Exposure response may be characterized by acquiring preview frames at varying duty cycles of the illumination assembly (100), thereby constructing a device-specific curve used to select shutter speed and gain during runtime. Lens spacing defined by the lens-holder bar (300) and lens mount (302) can be validated by imaging a resolution chart to confirm that the specified working distance yields sharp fundus detail.

These procedures support consistent optical geometry and imaging quality across production units. Opto-mechanical alignment can be verified against a printed target to estimate angular and lateral deviation of the camera/illumination axis relative to the optical axis. Units meeting angular deviation within about 5 degrees and lateral offset within about 5 millimeters at a working distance of about 40-60 millimeters have been found to yield stable reflex capture and fundus imaging in practice; the measured offsets may be stored as per-unit correction factors. The electronics compartment (103) provides internal retention for the processor (106), power bank (104), and display (108), while the headset shell (112) constrains optical alignment. The rear cover (214) and outer shell (210) provide exterior structural housing that maintains this alignment across repeated use and assembly.

Data Handling, Security, and Safety

Captured images and model outputs may be stored locally with associated timestamps and device identifiers. When network functions are enabled, data may be transmitted over encrypted communication channels for remote review. Model and firmware update packages are digitally signed prior to installation to prevent tampering.

Safety controls implemented in firmware regulate the intensity and duty cycle of the illumination assembly (100) and enforce capture lockouts to maintain exposures within safe limits. Electronic subsystems including the embedded processor (106), power bank (104), and display (108) are retained within the electronics compartment (103), enclosed by the headset shell (112) and outer shell (210) to ensure mechanical stability and safe operation. Mechanical features of the headset assembly (200), together with adjustable fit elements, enable comfortable alignment for both pediatric and adult subjects. Alignment cues presented on the display (108) guide non-specialist users to achieve proper coaxial positioning.

Examples and Performance (Non-Limiting)

In representative leukocoria development, a curated dataset consisting of 328 leukocoria pupil instances and 285 normal pupil instances was compiled, with augmentations expanding the dataset for training. Validation performance for the detector achieved overall precision near 95 percent, recall near 94 percent, and mean average precision near 98 percent. After retraining with images simulating smaller leukocoria, the detector achieved overall precision near 93 percent, recall near 90 percent, and mean average precision near 96 percent. In physical testing with an eye prosthesis, the headset assembly (200) detected simulated leukocoria down to approximately one millimeter in diameter while correctly identifying normal controls.

For retinal analysis, datasets of normal and retinoblastoma fundus images were used to train both object detection and classification models. The detection model localized the optic disc and retinoblastoma with performance including mean average precision of approximately 96 percent, and a ResNet-50 classifier achieved approximately 97 percent overall accuracy in validation. These studies also demonstrated clinical capture of diagnostic retinal images without pharmacologic dilation by employing infrared preview from the illumination assembly (100) followed by synchronized white-light capture through the camera (102) and diopter lens (114).

These examples are presented to demonstrate feasibility and utility and are not intended to limit the scope of the claimed invention to specific datasets, metrics, or performance thresholds.

Alternative Embodiments

The camera (102) may be implemented using any suitable CMOS or CCD sensor responsive to visible and infrared wavelengths. The illumination assembly (100) may be configured as a coaxial ring LED, a segmented array with independently controllable elements, or a fiber-coupled light source. The diopter lens (114) may assume optical powers other than 20 diopters and may be retained by inserts of varying diameter within the lens mount (302).

The overall form factor may be realized as a handheld instrument or as a smartphone-coupled accessory in which the host device provides processing and display, while a rigid shell maintains coaxial alignment of the optics. Alternative processing configurations may include model ensembles, distilled network backbones, or dedicated hardware accelerators to meet computational and latency requirements.

The same hardware and software pipelines may be adapted to detect additional retinal pathologies, including but not limited to retinal detachment, hemorrhage, hemangioma, macular degeneration, Coats' disease, diabetic retinopathy, hypertensive retinopathy, and retinopathy of prematurity, provided that training datasets are available.

Computer-Implemented Aspects

In some embodiments, a non-transitory computer-readable medium stores instructions that, when executed by one or more processors such as the embedded processor (106), cause the device to perform a coordinated sequence of operations. These operations include controlling the illumination assembly (100) to provide both infrared preview and synchronized white-light exposure, acquiring extraocular pupil images with the camera (102) as shown in FIG. 2, and capturing retinal images through the diopter lens (114) positioned by the optical extension comprising the lens-holder bar (300) and the lens mount (302) as shown in FIGS. 3, 6, and 7.

The instructions further execute one or more object-detection networks and convolutional neural network classifiers to infer leukocoria and retinal abnormalities. Alignment cues and bounding-box overlays are generated and rendered on the display (108), while captured images, inference outputs, and associated metadata including timestamps and device identifiers are stored locally. When network functions are enabled, the data may be encrypted and transmitted over secure channels for remote review.

In further embodiments, the processor (106), together with the power bank (104) and the display (108), is retained within the electronics compartment (103), which is enclosed by the headset shell (112) and the outer shell (210). The processor (106) is further configured to receive and install digitally signed update packages for models and firmware, thereby maintaining system integrity, preventing tampering, and ensuring that analytic pipelines remain up to date and trustworthy.

Industrial Applicability and Advantages

The disclosed device is applicable to home screening, school-based screening, and primary-care triage in environments lacking ophthalmic specialists or pharmacologic dilation agents. The same assembly also functions as a portable, non-mydriatic fundus camera.

By enforcing coaxial alignment among the illumination assembly (100), the camera (102), and the subject's eye (110) within the rigid headset shell (112) and outer shell (210), and by sequencing infrared preview with synchronized white-light capture through the diopter lens (114), the system achieves a consistent red-reflex geometry. This design reduces angle-dependent errors common in ad-hoc smartphone imaging.

On-device inference executed by the embedded processor (106) provides immediate results with bounding-box overlays and explainable outputs on the display (108). The processor (106), display (108), and power bank (104) are retained within an electronics compartment (103) that is enclosed by the headset shell (112) and outer shell (210), ensuring safe and stable operation during mobile use.

The absence of pharmacologic dilation requirements permits imaging in low-resource environments, while the compact design with rechargeable power and a rear cover (214) supports mobile deployment. The architecture therefore addresses the need for low-cost, accessible, and reliable screening tools across both developed and underserved healthcare contexts.

What is claimed is:

1. An integrated ocular imaging screening system comprising:

a headset assembly including a housing configured to be worn by a user and to position (i) a camera module and (ii) an illumination assembly so that respective optical axes of the camera module and the illumination assembly are substantially coincident with each other and with an optical axis of a subject's eye when the housing is placed against a periorbital region, thereby enabling capture of extraocular pupil images under red-reflex examination conditions;

a removable optical extension detachably coupled to the housing, the removable optical extension including a lens-holder bar that establishes a fixed working distance and a lens mount retaining a diopter lens positioned on the substantially coincident optical axes such that, when the removable optical extension is attached, the camera module captures non-mydriatic fundus images through the diopter lens;

at least one embedded processor within the housing configured to:

(i) control an infrared preview illumination to frame the fundus prior to capture;

(ii) trigger a white-light exposure synchronized to a camera integration period to acquire a color fundus image without pharmacologic dilation;

(iii) execute at least a first machine-learning model on the extraocular pupil images to detect leukocoria;

(iv) in response to detecting leukocoria, execute at least a second machine-learning model on the non-mydriatic fundus images to determine a presence of an intraocular abnormality;

and a display configured to render alignment guidance for extraocular capture and to render an explainable overlay on the color fundus image indicating a localized region corresponding to the intraocular abnormality.

2. The system of claim 1, wherein the headset assembly comprises a thermoplastic housing fabricated by additive manufacturing and shaped to maintain coaxial alignment while providing lightweight portability and user comfort.

3. The system of claim 1, wherein the camera module comprises an image sensor responsive to visible and near-infrared wavelengths.

4. The system of claim 1, wherein the illumination assembly comprises infrared and white-light emitting elements positioned coaxially with the camera module.

5. The system of claim 1, wherein the embedded processor comprises a single-board computer integrated with a local display for real-time review of captured images and inference results.

6. The system of claim 1, further comprising a rechargeable power supply configured to enable portable operation without an external power source.

7. The system of claim 1, wherein the optical geometry is configured to replicate red-reflex examination conditions by maintaining illumination and camera alignment with the pupil to optimize leukocoria detection.

8. The system of claim 1, wherein the camera captures non-mydriatic retinal images.

9. A method for ocular screening and non-mydriatic retinal imaging using a wearable device, comprising:

placing a headset housing of the wearable device against a periorbital region so that a camera module and an illumination assembly are coaxial with a pupil of a subject's eye;

capturing, with the camera module, one or more extraocular pupil images under red-reflex examination conditions;

executing, on an embedded processor of the wearable device, a first machine-learning model on the one or more extraocular pupil images to detect leukocoria;

in response to detecting leukocoria, detachably coupling to the headset housing a removable optical extension that positions a diopter lens on the same optical axis as the camera module and the illumination assembly and establishes a fixed working distance for fundus imaging;

operating an infrared preview illumination to center a fundus;

triggering a white-light pulse synchronized to a camera exposure to obtain a color, non-mydriatic fundus image without pharmacologic dilation;

executing, on the embedded processor, a second machine-learning model on the color fundus image to determine a presence of an intraocular abnormality and rendering an explainable overlay indicating a localized region corresponding to the intraocular abnormality on a local display of the wearable device.

* * * * *